United States Patent [19]

Sasagawa et al.

[11] Patent Number: 4,980,497
[45] Date of Patent: Dec. 25, 1990

[54] MONOMER OF CARBONATE ESTER HAVING ISOPROPENYLPHENYL GROUP

[75] Inventors: Katsuyoshi Sasagawa; Yoshinobu Kanemura; Masao Imai; Toshiyuki Suzuki, all of Kanagawa, Japan

[73] Assignee: Mitsui Toatsu Chemicals, Inc., Tokyo, Japan

[21] Appl. No.: 362,338

[22] Filed: Jun. 6, 1989

[30] Foreign Application Priority Data

Jun. 9, 1988 [JP] Japan ................. 63-140483
Mar. 7, 1989 [JP] Japan ................. 64-52893
Mar. 17, 1989 [JP] Japan ................. 64-63509

[51] Int. Cl.$^5$ .......................... C07L 271/08
[52] U.S. Cl. ........................ 560/33; 548/231; 526/301; 560/357
[58] Field of Search ............ 560/33, 225, 357, 355

[56] References Cited

U.S. PATENT DOCUMENTS

| | | | |
|---|---|---|---|
| 2,958,704 | 11/1960 | Dinbergs et al. | 560/33 |
| 4,279,833 | 7/1981 | Culbertson | 560/33 |
| 4,504,628 | 3/1985 | Johnson | 560/33 |
| 4,604,439 | 8/1986 | Colvin et al. | 326/288 |
| 4,633,010 | 12/1986 | Sinch et al. | 560/355 |

FOREIGN PATENT DOCUMENTS 185606 6/1986 European Pat. Off.
345748 12/1989 European Pat. Off.
2063248 6/1981 United Kingdom ............ 560/33

Primary Examiner—Donald G. Daus
Attorney, Agent, or Firm—Burns, Doane, Swecker & Mathis

[57] ABSTRACT

Polyfunctional monomers are disclosed that yield transparent resins having high transparency and excellent surface hardness and heat resistance. The present polyfunctional monomers are represented by the general formula (I):

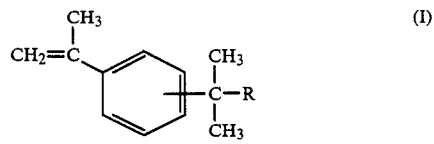

wherein R represents a group having a carbamido group or an oxazolidone group that will be bonded to the dimethylbenzyl group of the formula (I) and an acryl group or methacryl group at the other end. Control of the polymerization of the polyfunctional monomers is easy, and polymerization of the polyfunctional monomers yield and resins having excellent surface hardness, heat resistance, and workability, and having high transparency. The resins are well adapted for use as glazing materials, optical lenses, and optical disc substrates.

1 Claim, No Drawings

MONOMER OF CARBONATE ESTER HAVING ISOPROPENYLPHENYL GROUP

BACKGROUND OF THE INVENTION

1. Field of the invention

The present invention relates to novel polyfunctional monomers useful as starting material for the production of transparent resins.

2. Description of the Prior Art

Transparent resins are generally light in weight and excellent in impact resistance, workability, and mass-productivity in comparison to inorganic glasses, and are used, for example, as vehicle windows, light-covers, indoor notice boards, and skylights.

The synthetic resins mainly used for these applications are for example, polymethyl methacrylate, polystyrene, and polycarbonate, as well as polydiethylene glycol bisallyl carbonate.

The present inventors have investigated the use of transparent resins for parts pertaining to vehicle components such as car windows, and have discovered that polymethyl methacrylate, polystyrene, and polycarbonate have problems in that the surface hardness of these products is low, the resin surface is susceptible to marring, and they are poor in heat resistance. Accordingly, the present inventors have studied intensively to solve these problems.

SUMMARY OF THE INVENTION

The present invention overcomes the problems and disadvantages of the prior art by providing a new class of monomers from which hard transparent resins can be prepared that are not attended by the disadvantages discussed above.

An object of the invention is to provide polyfunctional monomers that can be used as starting materials for production of transparent resins having high transparency, excellent surface hardness, and heat resistance.

A further object of the present invention is to provide polyfunctional monomers whose polymerization conditions are easy to select.

A still further object of the invention is to provide a process for production of the polyfunctional monomers.

Additional objects and advantages of the invention will be apparent from the description that follows, or may be learned by practicing the invention.

To achieve the objects and in accordance with the purpose of the invention, as embodied and broadly described herein, the present invention provides a polyfunctional monomer of the general formula (I):

$$CH_2=C(CH_3)-C_6H_4-C(CH_3)_2-R \quad (I)$$

wherein R is selected from the group consisting of $$-N(H)-CO-CH(R_1)-CH_2OC(=O)-C(R_2)=CH_2,$$

$$-N(H)-CO-CH[CH_2OC(=O)-C(R_3)=CH_2][CH_2OC(=O)-C(R_4)=CH_2],$$

$$-N(H)-CO-CH_2-C(CHO)[CH_2OC(=O)-C(R_5)=CH_2][CH_2OC(=O)-C(R_6)=CH_2],$$

$$-N(H)-COCH_2-C[CH_2OC(=O)-C(R_7)=CH_2][CH_2OC(=O)-C(R_8)=CH_2][CH_2OC(=O)-C(R_9)=CH_2] \text{ and }$$

$$-N<(CH_2CHCH_2OC(=O)-C(R_{10})=CH_2)(C(=O)O)>$$

and wherein $R_1$ to $R_{10}$ each represents hydrogen or a methyl group.

The present invention also provides a process for producing the polyfunctional monomers, comprising reacting 3-isopropenyl-α,α-diemthylbenzyl isocyanate or 4-isopropyenyl-α,α-dimethylbenzyl isocyanate with various mono-, di- and tri-acrylate esters, depending on the structure of the desired product.

DETAILED DESCRIPTION OF THE INVENTION

Reference will now be made in detail to the present preferred embodiments of the invention.

The first group of the present novel polyfunctional monomers comprises a difunctional monomer represented by the general formula (II):

$$CH_2=C(CH_3)-C_6H_4-C(CH_3)_2-N(H)-CO-CH(R_1)-CH_2OC(=O)-C(R_2)=CH_2 \quad (II)$$

wherein $R_1$ and $R_2$ each represent hydrogen or a methyl group.

Specific and non-limiting examples thereof include N-(3-isopropenyl-α, α-dimethylbenzyl)-2-acryloyloxyethyl methacryloyloxyethyl carbamate, N-(4-isopropenyl-2-methacryloyloxyethyl carbamate, N-(4-isopropenyl-α,α-dimethylbenzyl)-2-acryloyloxyethyl carbamate, N-(4-isopropenyl-α,α-dimethylbenzyl)-2-methacryloyloxyethyl carbamate, N-(3-isopropenyl-α,α-dimethylbenzyl)-1-acryloyloxypropan-2-yl carbamate, N-(3-isopropenyl-α,α-dimethylbenzyl)-1- methacryloyloxypropan-2-yl carbamate, N-(4-isopropenyl-α,α- dimethylbenzyl)-1-methacryloyloxypropan-2-yl carbamate.

These compounds can be produced by reacting a compound selected from the group consisting of 3-isopropenyl-α,α-dimethylbenzyl isocyanate and 4-isopropenyl-α,α-dimethylbenzyl isocyanate with a compound selected from the group consisting of 2-hydroxyethyl acrylate, 2-hydroxyethyl methacrylate, 2-hydroxypropyl acrylate and 2-hydroxypropyl methacrylate. Optionally, the reaction may be conducted in a solvent or without solvent and optionally in the presence of a urethanization-promoting catalyst.

The above reaction is carried out such that 1 to 1.2 mol, preferably 1 to 1.05 mol, of 2-hydroxyethyl acrylate, 2-hydroxyethyl methacrylate, 2-hydroxypropyl acrylate or 2-hydroxypropyl methacrylate is added to 1 mol of 3-isopropenyl-α,α-dimethylbenzyl isocyanate or 4-isopropenyl-α,α-dimethylbenzyl isocyanate. Preferably, the reaction is carried out in a solvent that will not react with the reagents, such as hexane, benzene, or toluene. The reaction temperature is kept at from about 25 to about 110° C., preferably from about 40° to about 65° C., to allow the reaction to proceed. Optionally, a urethanization-promoting catalyst such as dibutyl tin dilaurate is added in an amount of from about 0.1 to about 5 wt. %, preferably from about 0.5 to about 3 wt. %, based on the weight of the isocyanate. After the reaction is complete, the reaction medium is purified by chromatography to produce a difunctional carbamic acid ester according to the present invention.

The second group of the present novel polyfunctional monomers comprises a polyfunctional monomer selected from the group consisting of monomers represented by the general formulae (III), (IV) and (V):

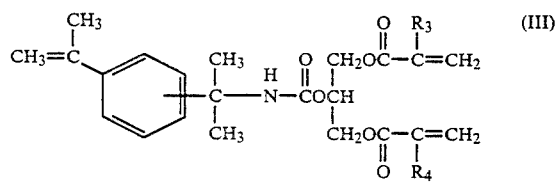

wherein $R_3$ and $R_4$ each represent hydrogen or a methyl

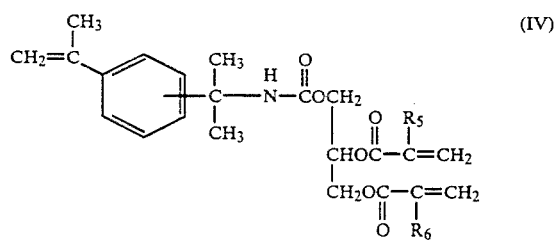

wherein $R_5$ and $R_6$ each represent hydrogen or a methyl group, and

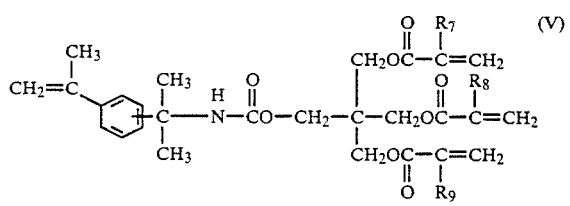

wherein $R_7$, $R_8$, and $R_9$ each represent hydrogen or a methyl group.

Specific and non-limiting examples thereof include N-(3-isopropenyl-α,α-dimethylbenzyl)-1,3-diacryloyloxypropan2-yl carbamate, N-(3-isopropenyl-α,α-dimethylbenzyl)-1-acryloyloxy-3-methacryloyloxypropan-2-yl carbamate N-(3-isopropenyl-α,α-dimethylbenzyl)-1,3-dimethacryloyloxypropan2-yl carbamate, N-(4-isopropenyl-α,α-dimethylbenzyl)-1 3-diacryloyloxypropan-2-yl carbamate, N-(4-isopropenyl-α,αdimethylbenzyl)-1-acryloyloxy-3-methacryloyloxypropan-2-yl carbamate, N-(4-isopropenyl-α,α-dimethylbenzyl)-1,3-dimethacryloyloxypropan-2-yl carbamate, N-(3-isopropenyl-α,α-dimethylbenzyl)-2,3-diacryloyloxypropan-1-yl carbamate N-(3-isopropenyl-α,α-dimethylbenzyl)-2-acryloyloxy-3-methacryloyloxypropan-1-yl carbamate, N-(3-isopropenyl-α,αdimethylbenzyl)-2,3-dimethacryloyloxy-1-yl carbamate, N-(4-isopropenyl-α,α-dimethylbenzyl)-2,3-diacryloyloxypropan-1-yl carbamate, N-(4-isopropenyl-α,α-dimethylbenzylα,α)-2-acryloyloxy-3-methacryloyloxypropan-1-yl carbamate, N-(4-isopropenyl-α,α-dimethylbenzyl)-2,3-dimethacryloyloxy-1-yl carbamate, N-(3-isopropenyl-α,α-dimethylbenzyl)-2,2-diacryloyloxymethyl-3-acryloyloxypropyl carbamate N-α,α(3-isopropenyl-α,α-dimethylbenzyl)-2,2-dimethacryloyloxymethyl3-methacryloyloxydipropyl carbamate, N-(4-isopropenyl-α,α-dimethylbenzyl)-2,2-diacryloyloxymethyl-3-acryloyloxypropyl carbamate, and N-(4-isopropenyl-α,α-dimethylbenzyl)-2,2-dimethacryloyloxymethyl-3-methacryloyloxypropyl carbamate.

These compounds can be produced by conducting a urethanization reaction of 3-isopropenyl-α,α-dimethylbenzyl isocyanate or 4-isopropenyl-α,α-dimethylbenzyl isocyanate with glycerol diacrylate, glycerol acrylate methacrylate, glycerol dimethacrylate, pentaerythritol triacrylate or pentaerythritol trimethacrylate, pentaerythritol acrylate dimethacrylate, pentaerythritol methacrylate diacrylate. Optionally, a solvent for the reagents may be or may not be used and optionally the reaction is effected in the presence of a urethanization-promoting catalyst.

The above reaction is carried out such that from about 1 to about 1.2 mol, preferably from about 1 to about 1.5 mol, of glycerol diacrylate, glycerol acrylate methacrylate, glycerol dimethacrylate, pentaerythritol triacrylate or pentaerythritol trimethacrylate is added to about 1 mol of 3-isopropenyl-α,α-dimethylbenzyl isocyanate or 4-isopropenyl-α,α-dimethylbenzyl isocyanate. Preferably, the reaction is carried out in a solvent that will not react with the reagents, such as hexane, benzene, and toluene. The temperature of the reaction medium is kept at from about 25 to about 110 ° C., preferably from about 40 to about 65 ° C., and optionally a urethanization-promoting catalyst such as dibutyl tin dilaurate is added in an amount of 0.1 to 5 wt. %, preferably 0.5 to 3 wt. %, based on the weight of the isocyanate.

After the reaction is complete, the reaction medium is purified by chromatography to yield a polyfunctional carbamic ester monomer according to the present invention.

The third group of the present novel polyfunctional monomers comprises a difunctional monomer represented by the general formula (VI):

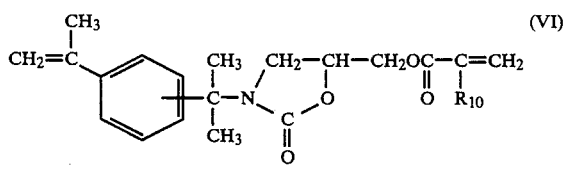

wherein $R_{10}$ represents hydrogen or a methyl group.

Specific and non-limiting examples thereof include N-(3-isopropenyl-α,α-dimethylbenzyla,α)-5-acryloyloxymethylene-N-(4-isopropenyl-α,α-dimethylbenzyl)-5-acryloyloxymethylene-2-oxazolidone, N-(3-isopropenyl-α,α-dimethylbenzyl)-5-methacryloyloxymethylene-2-oxazolidone, and N-(4-isopropenyl-α,α-dimethylbenzyl)-5-methacryloyloxymethylene-2-oxazolidone These compounds are produced by adding from about 0.8 to about 1.20 mol, preferably from about 0.95 to 1.05 mol of glycidyl acrylate or glycidyl methacrylate dropwise to 1 mol of 3-isopropenyl-α,α-dimethylbenzyl isocyanate 4-isopropenyl-α,α-dimethylbenzyl isocyanate in a solvent that will not react with the reagents such as benzene, toluene or xylene. The reaction is carried out in the presence of an oxazolidone-producing reaction catalyst such as tributylphosphine oxide-lithium bromide, in an amount of from about 1.0 to about 10 mol %, preferably from about 1.5 to about 5.0 mol %, relative to the 3-isopropenyl-α,αdimethylbenzyl isocyanate or 4-isopropenyl-α,αdimethylbenzyl isocyanate. The temperature of the reaction medium is kept at from about 70° to about 150° C., preferably from about 90 to about 120 ° C., so as to allow the reaction to proceed. After the reaction is complete, the reaction medium is purified by chromatography to yield a difunctional monomer having the general formula (VI).

Since the present novel polyfunctional monomer has both a functional group whose polymerization speed is high and an isopropenyl group whose polymerization speed is low, where functional group and isopropenyl group will be homopolymerized or copolymerized with a monomer having an acryl group, a methacryl group, a vinylphenyl group, or the like, the control of polymerization is quite easy and a resin can be obtained that is highly transparent and at the same time has excellent surface hardness, heat resistance, and workability as regards severing and cutting thereof, in comparison to polymethyl methacrylate, polystyrene, polycarbonate, and polydiethylene glycol bisallyl carbonate. Selection of the polymerization conditions of the present monomer is easy. The present polyfunctional monomers are useful as starting materials for producing resins that are suitable for use as glazing materials, for example, for parts pertaining to vehicle's components such as car windows, and for optical elements such as optical disk substrates and lenses of spectacles and cameras.

EXAMPLES

The present invention will now be described more particularly with reference to the following Examples, but of course the present invention is not limited by the Examples. Other examples within the scope of the invention will be readily apparent to those skilled in the art from a reading of the present disclosure and from practicing the invention.

In the Examples, the parts quoted are parts by weight.

EXAMPLE 1

8.3 parts of 3-isopropenyl-α,α-dimethylbenzyl isocyanate, 10.0 parts of toluene, and 4.8 parts of 2-hydroxyethyl acrylate were mixed, and the resulting reaction was carried out for 5 hours with stirring while the temperature of the reaction medium was kept at 100 ° C. After the reaction was complete, the reaction medium was condensed. The condensed medium was purified by chromatography to yield 2.9 parts of N-(3-isopropenyl-α,α-dimethylbenzyl)-2-acryloyloxyethyl carbamate that was colorless and syrupy.

Elemental analysis figures (calculated for $C_{18}H_{23}NO_4$):

|  | C | H | N |
| --- | --- | --- | --- |
| Found (%) | 67.62 | 7.29 | 4.39 |
| Calculated (%) | 68.12 | 7.31 | 4.42 |

NMR (δ CDCl₃)

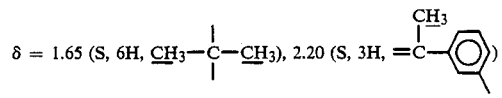

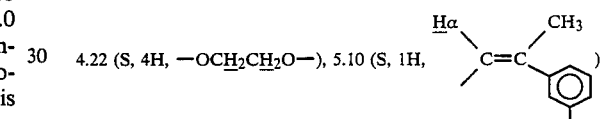

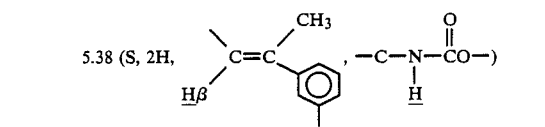

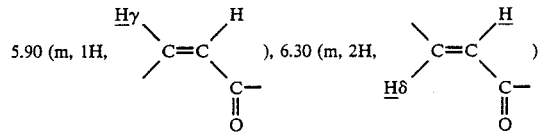

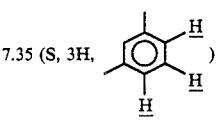

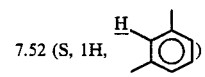

EXAMPLE 2

10.0 parts of 3-isopropenyl-α,α-dimethylbenzyl isocyanate, 6.5 parts of 2-hydroxyethyl methacrylate, and 0.1 part of dibutyl tin dilaurate (used as a urethanization reaction-promoting catalyst) were mixed, and the resulting reaction was carried out for 1 hour with stirring while the temperature of the reaction medium was kept at 65° C. After the reaction was complete, the reaction medium was purified by chromatography to yield 14.0 parts of N-(3-isopropenyl-α,α-dimethylbenzyl)-2-methacryloyloxyethyl carbamate that was colorless and syrupy.

Elemental analysis figures (calculated for $C_{19}H_{25}NO_4$):

|  | C | H | N |
|---|---|---|---|
| Found (%) | 68.77 | 7.32 | 4.28 |
| Calculated (%) | 68.86 | 7.61 | 4.23 |

NMR (δ CDCl₃)

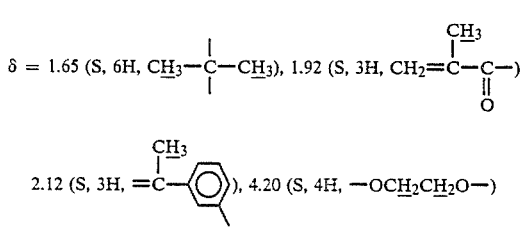

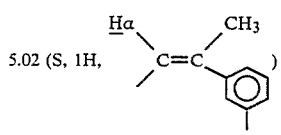

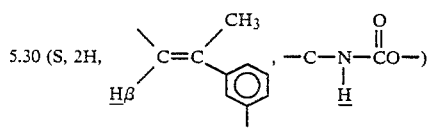

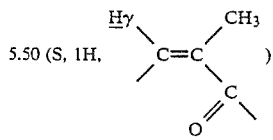

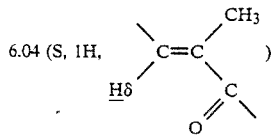

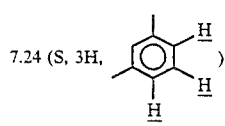

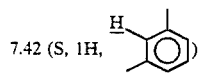

EXAMPLE 3

The procedure of Example 1 was repeated except that 8.3 parts of 4- isopropenyl-α,α-dimethylbenzyl isocyanate were used instead of 8.3 parts of 3-isopropenyl-α,α-dimethylbenzyl isocyanate, thereby producing 3.2 parts of N-(4-isopropenyl-α,α-dimethylbenzyl)-2-acryloyloxyethyl carbamate that was colorless and syrupy.

Elemental analysis figures (calculated for $C_{18}H_{23}NO_4$)

|  | C | H | N |
|---|---|---|---|
| Found (%) | 67.90 | 7.27 | 4.37 |
| Calculated (%) | 68.12 | 7.31 | 4.42 |

NMR (δ CDCl₃)

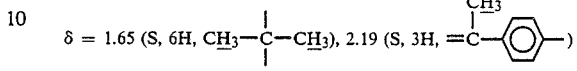

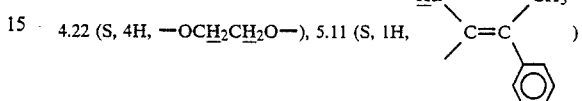

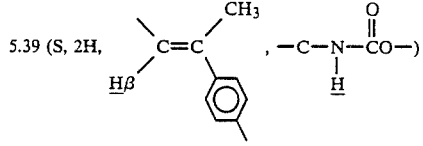

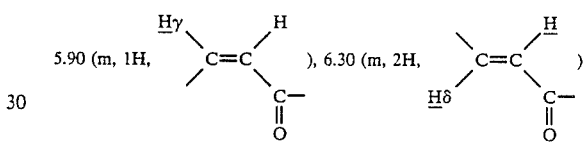

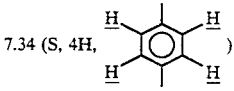

EXAMPLE 4

The procedure of Example 2 was repeated except that 10.0 parts of 4-isopropenyl-α,α-dimethylbenzyl isocyanate were used instead of 10.0 parts of 3-isopropenyl-α,αdimethylbenzyl isocyanate, thereby producing 14.2 parts of N-(4-isopropenyl-α,α-dimethylbenzyl)-2-methacryloyloxyethyl carbamate that was colorless and syrupy.

Elemental analysis figures (calculated for $C_{19}H_{25}NO_4$):

|  | C | H | N |
|---|---|---|---|
| Found (%) | 68.53 | 7.40 | 4.19 |
| Calculated (%) | 68.86 | 7.61 | 4.23 |

NMR (δ CDCl₃)

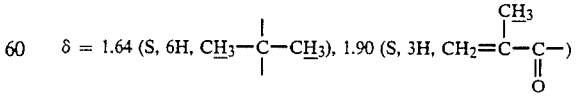

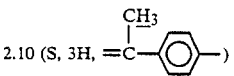

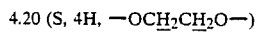

-continued 5.03 (S, 1H, Hα\C=C/CH3 with phenyl-CH3)

5.30 (S, 2H, Hβ\C=C/CH3 with p-tolyl, —C(=O)—N(H)—CO—)

5.52 (S, 1H, Hγ\C=C/CH3 with —C(=O)—)

6.06 (S, 1H, Hδ\C=C/CH3 with —C(=O)—)

7.34 (S, 4H, aromatic H's)

EXAMPLE 5

The procedure of Example 2 was repeated, except that 6.5 parts of 2-hydroxypropyl acrylate were used instead of 6.5 parts of 2-hydroxyethyl methacrylate, and the temperature of the reaction medium was maintained at 80° C. instead of 65° C., thereby producing 13.8 parts of N-(3-isopropenyl-α-dimethylbenzyl)-1-acryloyloxypropan-2-yl carbamate that was colorless and syrupy.

Elemental analysis figures (calculated for $C_{19}H_{25}NO_4$):

|  | C | H | N |
|---|---|---|---|
| Found (%) | 68.66 | 7.53 | 4.29 |
| Calculated (%) | 68.86 | 7.61 | 4.23 |

NMR (δ CDCl₃)

δ = 1.26 (m, 3H, —COCHCH₂—), 1.68 (S, 6H, CH₃—C(CH₃)—)

2.18 (S, 3H, =C(CH₃)—Ar—), 4.10 (m, 2H, —COCHCH₂—)

5.12 (m, 2H, Hα\C=C/CH3 with aryl, —COCHCH₂—)

-continued 5.41 (m, 2H, Hβ\C=C/CH3 with p-tolyl, —C(=O)—N(H)—CO—)

5.82 (m, 1H, Hγ\C=C/H with —C(=O)O—), 6.35 (m, 2H, \C=C/H Hδ with —C(=O)O—)

7.36 (S, 3H, aromatic)

7.55 (S, 1H, aromatic)

EXAMPLE 6

The procedure of Example 2 was repeated, except that 7.5 parts of 2- hydroxypropyl methacrylate were used instead of 6.5 parts of 2-hydroxyethyl methacrylate, the temperature of the reaction medium was maintained at 80° C. instead of 65° C., and the amount of the dibutyl tin laurate used was 0.2 part instead of 0.1 part, thereby producing 15.1 parts of N-(3-isopropenyl-α,α-dimethylbenzyla,α}-1-methacryloyloxypropan-2-yl carbamate that was colorless and syrupy.

Elemental analysis figures (calculated for $C_{20}H_{27}NO_4$):

|  | C | H | N |
|---|---|---|---|
| Found (%) | 69.45 | 7.71 | 4.01 |
| Calculated (%) | 69.54 | 7.87 | 4.05 |

NMR (δ CDCl₃)

δ = 1.24 (m, 3H, —COCHCH₂—), 1.66 (S, 6H, CH₃—C(CH₃)—CH₃)

1.96 (S, 3H, CH₂=C(CH₃)—C(=O)—)

2.17 (S, 3H, =C(CH₃)—Ar—), 4.08 (d, 2H, —COCHCH₂—)

5.10 (m, 2H, Hα\C=C/CH3 with aryl-CH3, —COCHCH₂—)

5.40 (S, 2H, Hβ\C=C/CH3 with p-tolyl, —C(=O)—N(H)—CO—)

5.60 (S, 1H, 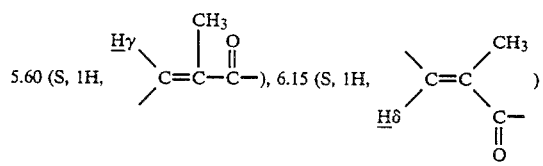), 6.15 (S, 1H, 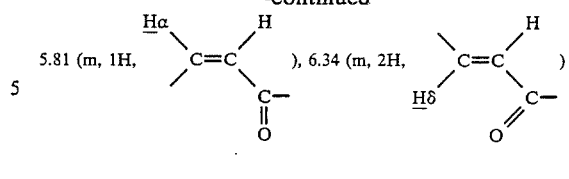)

7.34 (S, 3H, 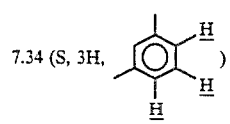)

7.54 (S, 1H, 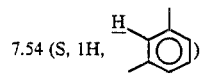)

EXAMPLE 7

10.0 parts of 4-isopropenyl-α,α-dimethylbenzyl isocyanate, 6.7 parts of 2-hydroxypropyl acrylate, 10.0 parts of benzene, and 0.5 part of dibutyl tin dilaurate (used as a reaction-promoting catalyst) were mixed, and the resulting reaction was carried out for 5 hours with stirring while the temperature of the reaction medium was kept at 60° C. After the reaction was complete, the reaction medium was purified by chromatography to yield 12.8 parts of N-(4-isopropenyl-α,α-dimethylbenzyl)-1-acryloyloxypropan-2-carbamate that was colorless and syrupy.

Elemental analysis figures (calculated for $C_{19}H_{25}NO_4$ α,α)

|  | C | H | N |
|---|---|---|---|
| Found (%) | 68.45 | 7.44 | 4.07 |
| Calculated (%) | 68.86 | 7.61 | 4.23 |

NMR (δ CDCl₃)

δ = 1.25 (d, 3H, −COCHCH₂−), 1.66 (S, 6H, CH₃−C−CH₃)

2.18 (S, 3H, 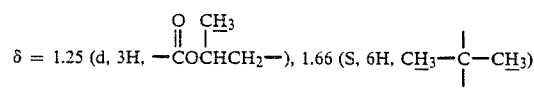), 4.12 (m, 2H, −COCHCH₂−)

5.12 (m, 2H, 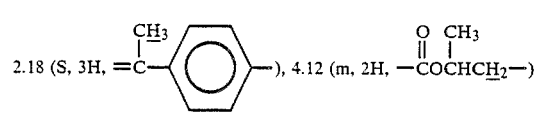, −COCHCH₂−)

5.40 (m, 2H, 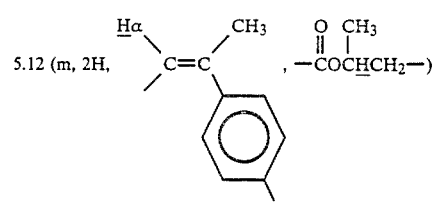, C−N−CO−)

5.81 (m, 1H, 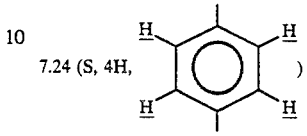), 6.34 (m, 2H, ...)

7.24 (S, 4H, ...)

EXAMPLE 8

12.0 parts of 3-isopropenyl-α,α-dimethylbenzyl isocyanate, 10.0 parts of toluene, and 11.9 parts of glycerol-1,3-diacrylate were mixed, and the resulting reaction was carried out for 3 hours with stirring while the temperature of the reaction medium was kept at 90° C. After the the reaction was complete, the reaction medium was condensed. The condensed medium was purified by chromatography to yield 2.4 parts of N-(3-isopropenyl-α,α-dimethylbenzyl)-1,3-diacryloyloxypropan-2-yl carbamate that was colorless and syrupy.

Elemental analysis figures (calculated for $C_{22}H_{27}NO_6$):

|  | C | H | N |
|---|---|---|---|
| Found (%) | 65.54 | 6.57 | 3.33 |
| Calculated (%) | 65.82 | 6.78 | 3.49 |

NMR (δ CDCl₃)

δ = 1.66 (s, 6H, CH₃−C−CH₃)

2.14 (s, 3H, 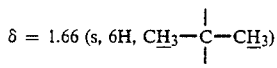)

4.36 (s, 4H, −CH₂OC−)

5.06 (s, 1H, )

5.15 (s, 1H, −COCH )

-continued 5.34 (s, 2H, 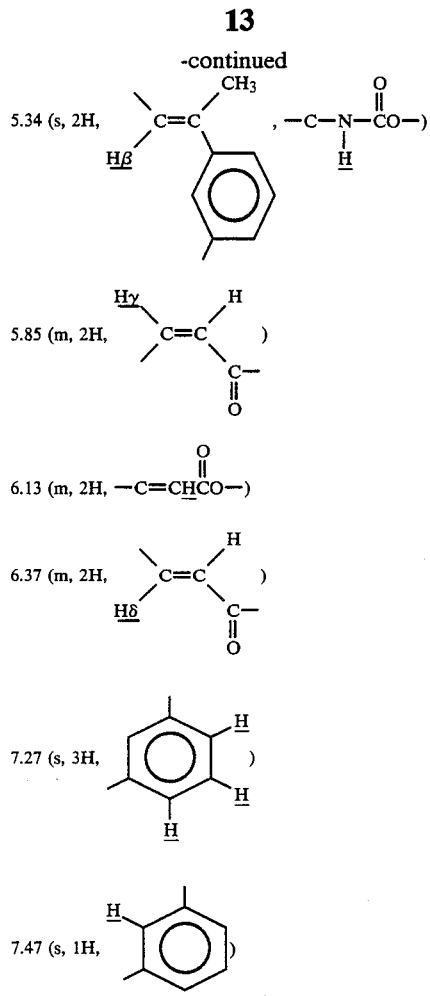

5.85 (m, 2H, ...)

6.13 (m, 2H, —C=CHCO—)

6.37 (m, 2H, ...)

7.27 (s, 3H, ...)

7.47 (s, 1H, ...)

EXAMPLE 9

48.0 parts of 3-isopropenyl-α,α-dimethylbenzyl isocyanate, 54.4 parts of glycerol-1,3-dimethacrylate, and 0.5 part of dibutyl tin dilaurate (used as a reaction promoting catalyst) were mixed, and the resulting reaction was carried out for 1 hour with stirring while the temperature of the reaction medium was kept at 60 ° C. After the reaction was complete, the reaction medium was purified by chromatography to yield 63.0 parts of N-(3-isopropenyl-α, α-dimethylbenzyl-1,3-dimethacryloyloxypropan-2-yl carbamate that was colorless and syrupy. Elemental analysis figures (calculated for $C_{24}H_{31}NO_6$)

|  | C | H | N |
|---|---|---|---|
| Found (%) | 66.90 | 7.13 | 3.09 |
| Calculated (%) | 67.11 | 7.27 | 3.26 |

NMR (δ CDCl₃)

δ = 1.66 (s, 6H, 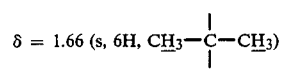)

1.92 (s, 6H, 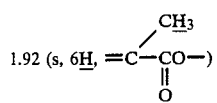)

-continued 2.13 (s, 3H, =C\\CH₃ ...)

4.25 (m, 4H, —CH₂OC—)
            ||
            O

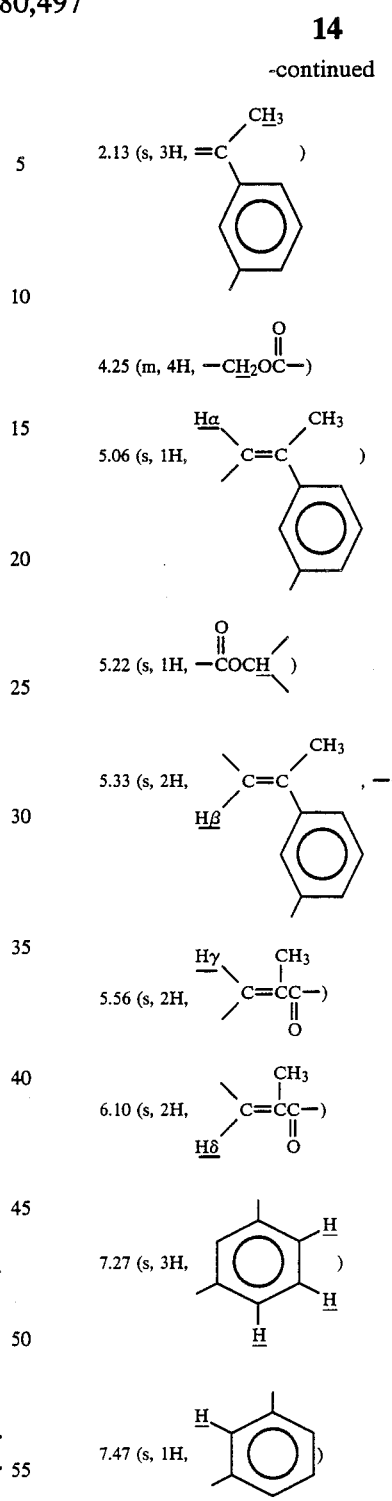

5.06 (s, 1H, ...)

5.22 (s, 1H, —COCH...)

5.33 (s, 2H, ...)

5.56 (s, 2H, ...)

6.10 (s, 2H, ...)

7.27 (s, 3H, ...)

7.47 (s, 1H, ...)

EXAMPLE 10

The procedure of Example 9 was repeated, except that 51.5 parts of glycerol-1-acrylate-3-methacrylate were used instead of 54.4 parts of glycerol-1,3-dimethacrylate, thereby producing 71.0 parts of N-(3-isopropenyl-α,α-dimethylbenzyl)-1-acryloyloxy-3-methacryloyloxypropan-2-yl carbamate that was colorless and syrupy.

Elemental analysis figures (calculated for $C_{23}H_{29}NO_6$):

|  | C | H | N |
|---|---|---|---|
| Found (%) | 66.11 | 6.99 | 3.23 |
| Calculated (%) | 66.49 | 7.04 | 3.37 |

NMR (δ CDCl₃)

δ = 1.67 (s, 6H, C<u>H</u>₃—C—C<u>H</u>₃) 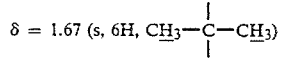

1.93 (s, 3H, =C<CH₃ / CO—) 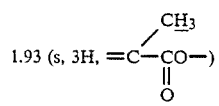

2.14 (s, 3H, =C<CH₃ / ) 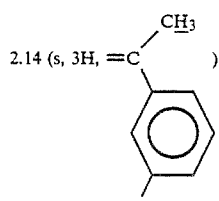

4.26 (m, 4H, —C<u>H</u>₂—OC—) 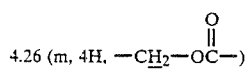

5.07 (s, 1H, Hα\C=C/CH₃ ) 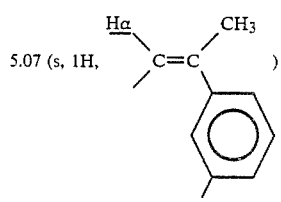

5.24 (s, 2H, —COC<u>H</u><, —C—N—CO) 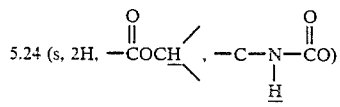

5.34 (s, 1H, \C=C/CH₃, Hβ) 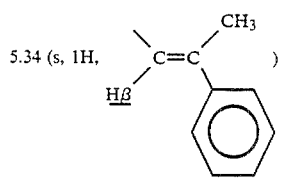

5.58 (s, 1H, Hγ\C=CC—/CH₃) 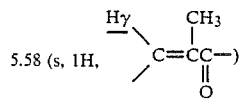

5.85 (m, 1H, Hε\C=C/H, C—) 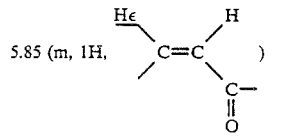

6.11 (m, 2H, —C=C<u>H</u>CO—, \C=CC—/CH₃, Hδ) 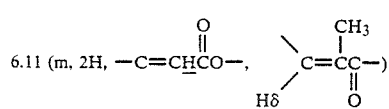

6.41 (m, 1H, 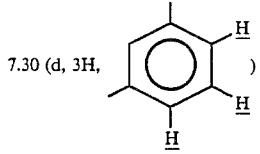 )

7.30 (d, 3H, 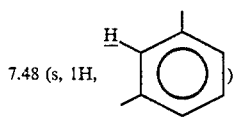 )

7.48 (s, 1H, 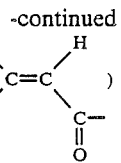 )

EXAMPLE 11

The procedure of Example 9 was repeated, except that 48.0 of parts of 4- isopropenyl-α,α-dimethylbenzyl isocyanate, and 47.8 parts of glycerol-1 3-diacrylate were used instead of 48.0 parts of 3-isopropenyl-α,α-dimethylbenzyl isocyanate, and 54.4 parts of glycerol-1 3dimethacrylate, respectively, thereby producing 62.1 parts of N-(4-isopropenyl-α,α-dimethylbenzyl)-1 3-diacryloyloxypropan-2-yl carbamate that was colorless and syrupy.

Elemental analysis figures (calculated for $C_{22}H_{27}NO_6$):

|  | C | H | N |
|---|---|---|---|
| Found (%) | 65.31 | 6.49 | 3.40 |
| Calculated (%) | 65.82 | 6.78 | 3.49 |

NMR (δ CDCl₃)

δ = 1.66 (s, 6H, C<u>H</u>₃—C—C<u>H</u>₃) 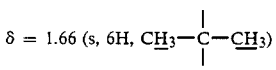

2.14 (s, 3H, =C<CH₃ / ) 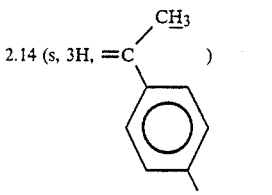

4.35 (s, 4H, —C<u>H</u>₂—CO—) 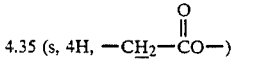

5.03 (s, 1H, Hα\C=C/CH₃ ) 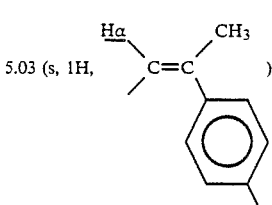

-continued 5.15 (s, 1H, 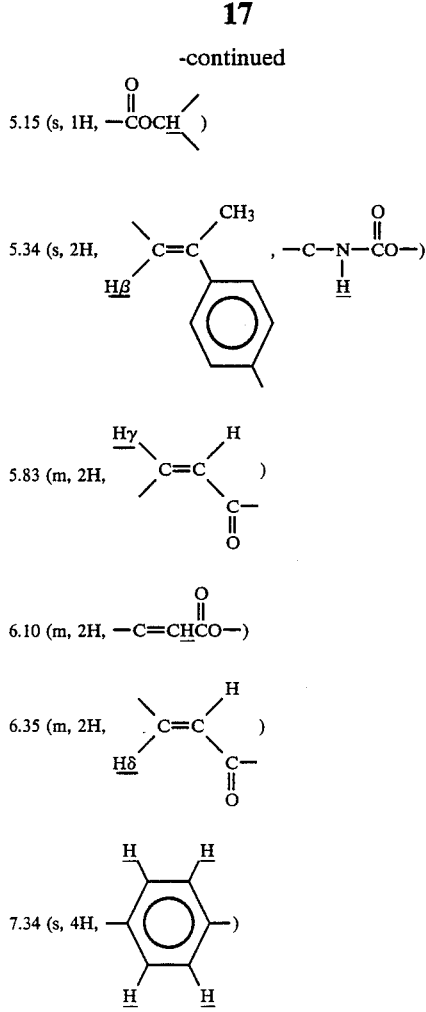)

5.34 (s, 2H, ...)

5.83 (m, 2H, ...)

6.10 (m, 2H, —C=CHCO—)

6.35 (m, 2H, ...)

7.34 (s, 4H, ...)

EXAMPLE 12

The procedure of Example 9 was repeated, except that 71.2 parts of pentaerythritol triacrylate were used instead of 54.4 parts of glycerol-1,3-dimethacrylate, thereby producing 50.2 parts of N-(3-isopropenyl-α,α-dimethylbenzyl)-2,2-diacryloyloxymethyl-3-acryloyloxypropyl carbamate that was colorless and syrupy.

Elemental analysis figures (calculated for $C_{27}H_{33}NO_8$):

|  | C | H | N |
|---|---|---|---|
| Found (%) | 64.19 | 6.37 | 2.80 |
| Calculated (%) | 64.92 | 6.66 | 2.80 |

NMR (δ CDCl₃)

$\delta$ = 1.66 (s, 6H, 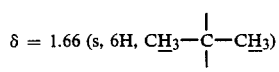)

-continued 2.16 (s, 3H, ...)

4.12 (s, 2H, CH₂—OCN—)

4.28 (s, 6H, —CH₂—OC—)

5.05 (s, 1H, ...)

5.38 (s, 2H, ...)

5.90 (m, 3H, ...)

6.30 (m, 6H, —C=CHCO—, ...)

7.35 (s, 3H, ...)

7.56 (s, 1H, ...)

EXAMPLE 13

The procedure of Example 9 was repeated, except that 48.0 parts of 4-isopropyl-α,αdimethylbenzyl isocyanate, and 81.3 parts of pentaerythritol trimethacrylate were used instead of 48.0 parts of 3-isopropenyl-α,-dimethylbenzyl isocyanate, and 54.4 parts of glycerol-1,3-dimethacrylate, respectively, thereby producing 77.1 parts of N-(4-isopropenyl-α,α-dimethylbenzyl)-2,2- dimethacryloyloxymethyl-3-methacryloyloxypropyl carbamate that was colorless and syrupy.

Elemental analysis figures (calculated for $C_{30}H_{39}NO_8$)

|              | C     | H    | N    |
|--------------|-------|------|------|
| Found (%)    | 66.11 | 7.00 | 2.50 |
| Calculated (%) | 66.53 | 7.26 | 2.59 |

NMR (δ CDCl₃)

δ = 1.66 (s, 6H, 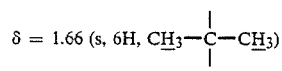)

1.90 (s, 9H, 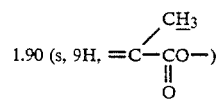)

2.11 (s, 3H, 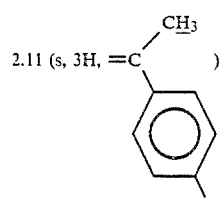)

4.10 (s, 2H, 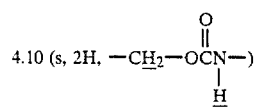)

4.23 (m, 6H, 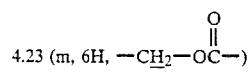)

5.05 (s, 1H, 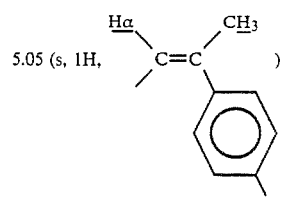)

5.30 (s, 2H, 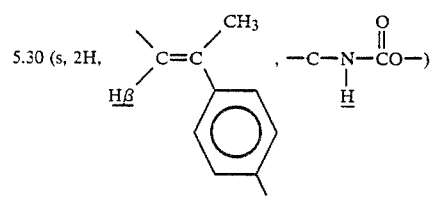)

5.54 (s, 3H, 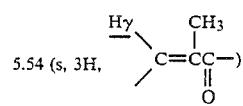)

6.09 (s, 3H, 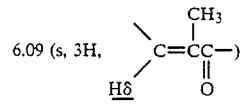)

7.37 (s, 4H, 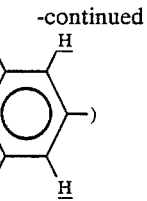)

EXAMPLE 14

The procedure of Example 8 was repeated, except that 11.9 parts of glycerol-2,3-diacrylate were used instead of 11.9 parts of glycerol-1,3-diacrylate, thereby producing 2.8 parts of N-(3-isopropenyl-α,α-dimethylbenzyl)-2,3-diacryloyloxypropan-1-yl carbamate that was colorless syrupy.

Elemental analysis figures (calculated for $C_{22}H_{27}NO_6$):

|              | C     | H    | N    |
|--------------|-------|------|------|
| Found (%)    | 65.69 | 6.46 | 3.31 |
| Calculated (%) | 65.82 | 6.78 | 3.49 |

NMR (δ CDCl₃)

δ = 1.68 (s, 6H, 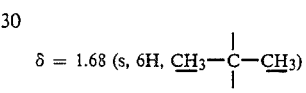)

2.17 (s, 3H, 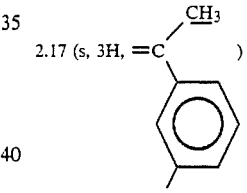)

4.32 (m, 4H, 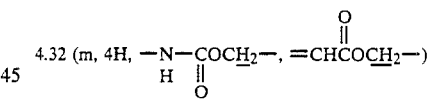)

5.08 (s, 1H, 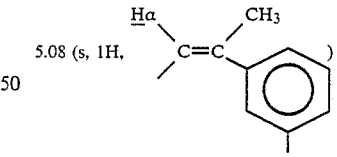)

5.21 (m, 1H, 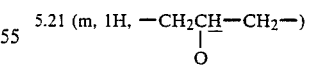)

5.34 (s, 1H, 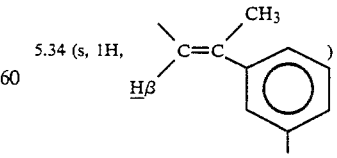)

5.87 (m, 2H, 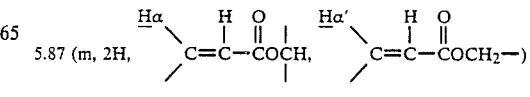)

6.14 (m, 2H, 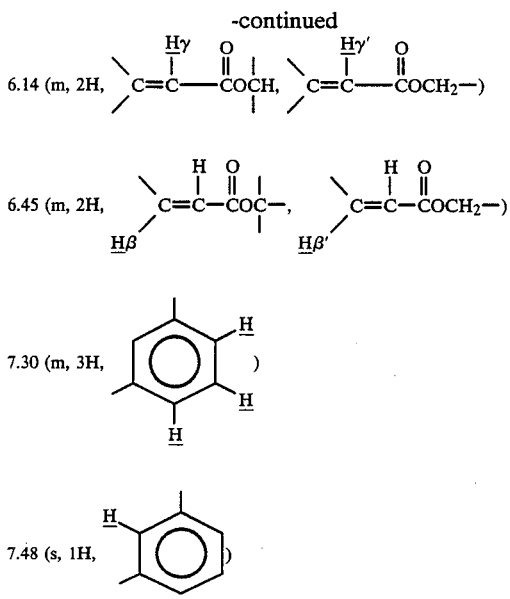

6.45 (m, 2H, 7.30 (m, 3H, 7.48 (s, 1H, )

EXAMPLE 15

20.0 parts of 3-isopropenyl-α,α-dimethylbenzyl isocyanate, 50.0 parts of toluene, 0.8 part of tributylphosphine oxide, and 0.2 part of lithium bromide were refluxed with stirring, and 12.9 parts of glycidyl acrylate were added dropwise thereto under reflux and the resulting reaction was allowed to proceed for 1 hour. After the reaction was complete, the reaction medium was condensed and purified by chromatography, thereby yielding 24.2 parts of N-(3-isopropenyl-α,α-dimethylbenzyl)-5-acryloyloxymethylene-2-oxazolidone that was colorless and watery.

Elemental analysis figures (calculated for $C_{19}H_{23}NO_4$):

|  | C | H | N |
|---|---|---|---|
| Found (%) | 68.92 | 6.91 | 4.37 |
| Calculated (%) | 69.28 | 7.04 | 4.25 |

NMR (δ/CDCl₃)

δ = 1.68 (s, 6H, C$\underline{H}_3$—C—C$\underline{H}_3$),

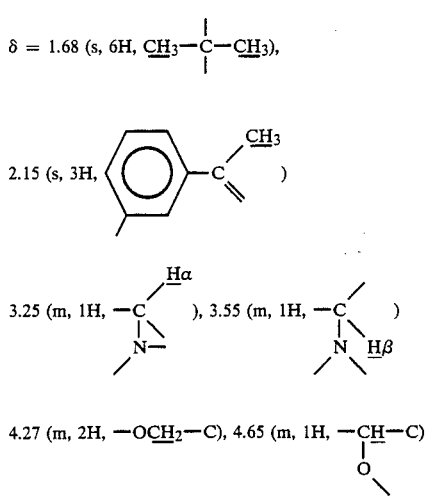

4.27 (m, 2H, —OC$\underline{H}_2$—C), 4.65 (m, 1H, —C$\underline{H}$—C)

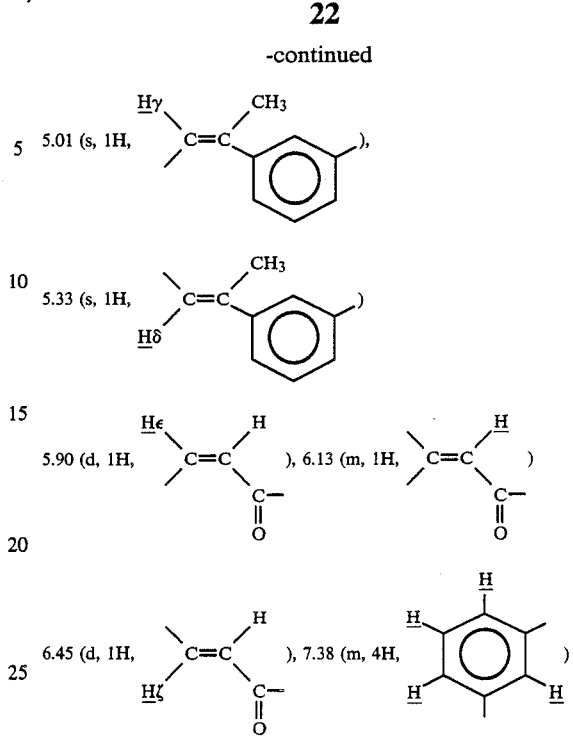

EXAMPLE 16

The procedure of Example 15 was repeated, except that 20.2 parts of 4-isopropenyl-α,α-dimethylbenzyl isocyanate were used instead of 20.2 parts of 3-isopropenyl-α,αdimethylbenzyl isocyanate, thereby producing 25.5 parts of N-(4-isopropenyl-α,α-dimethylbenzyl)-5-acryloyloxymethylene-oxazolidone 2-oxazolidone that was colorless and watery.

Elemental analysis figures (calculated for $C_{19}H_{23}NO_4$)

|  | C | H | N |
|---|---|---|---|
| Found (%) | 69.56 | 7.18 | 4.21 |
| Calculated (%) | 69.28 | 7.04 | 4.25 |

NMR (δ/CDCl₃)

δ = 1.68 (s, 6H, C$\underline{H}_3$—C—C$\underline{H}_3$),

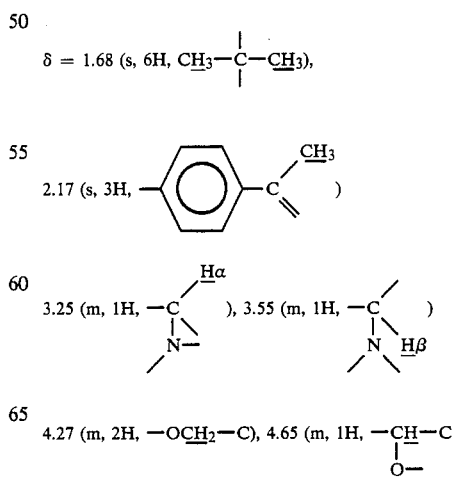

4.27 (m, 2H, —OC$\underline{H}_2$—C), 4.65 (m, 1H, —C$\underline{H}$—C)

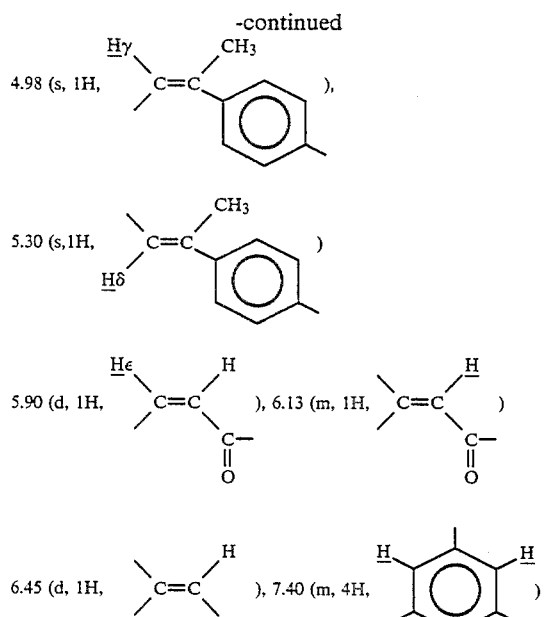

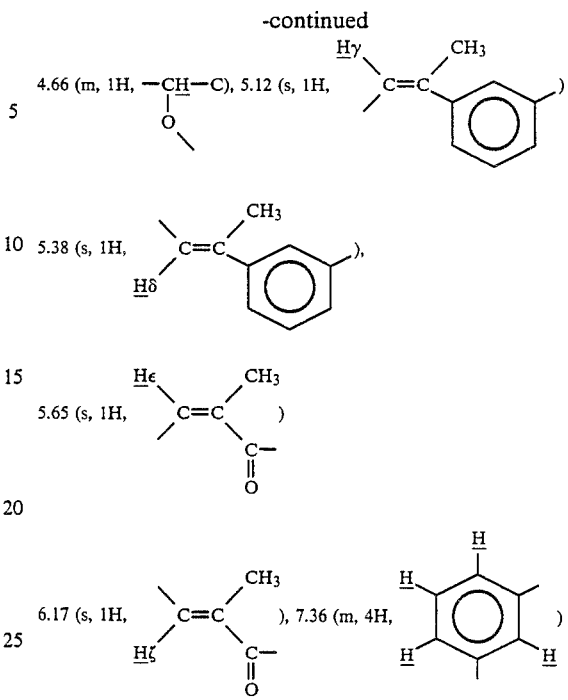

EXAMPLE 17

20.7 parts of 3-isopropenyl-α,α-dimethylbenzyl isocyanate, 50.0 parts of toluene, 0.8 parts of tributylphosphine oxide, and 0.2 part of lithium bromide were stirred under reflux, 14.2 parts of glycidyl methacrylate were added thereto dropwise, and the resulting reaction was allowed to proceed under reflux for 1 hour. After the reaction was complete, the reaction medium was condensed, and then was purified by chromatography to yield 30.6 parts of N-(3-isopropenyl-α,α-dimethylbenzyl)-5-methacryloyloxymethylene-2-oxazolidone that was colorless and watery.

Elemental analysis figures (calculated for $C_{20}H_{25}NO_4$):

|  | C | H | N |
|---|---|---|---|
| Found (%) | 70.16 | 7.05 | 4.23 |
| Calculated (%) | 69.95 | 7.34 | 4.08 |

NMR (δ/CDCl₃)

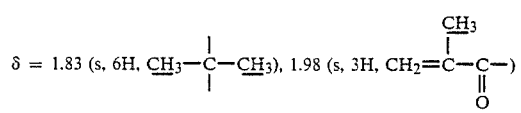

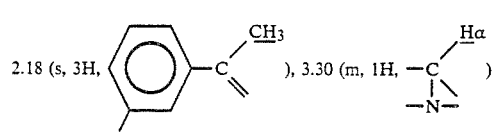

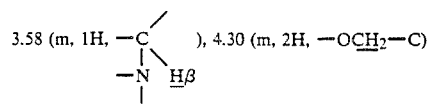

EXAMPLE 18

The procedure of Example 17 was repeated, except that 20.2 parts of 4-isopropenyl-α,α-dimethylbenzyl isocyanate were used instead of 20.02 parts of 3-isopropenyl-α,αdimethylbenzyl isocyanate, thereby producing 28.6 parts of N-(4-isopropenyl-α,α-dimethylbenzyl)-5-methacryloyloxymethylene-2-oxazolidone that was colorless and watery.

Elemental analysis figures (calculated for $C_{20}H_{25}NO_4$):

|  | C | H | N |
|---|---|---|---|
| Found (%) | 69.71 | 7.16 | 4.17 |
| Calculated (%) | 69.95 | 7.34 | 4.08 |

NMR (δ/CDCl₃)

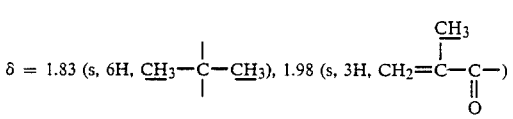

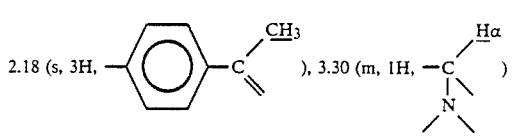

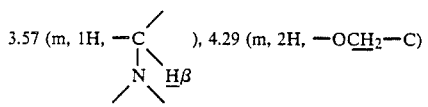

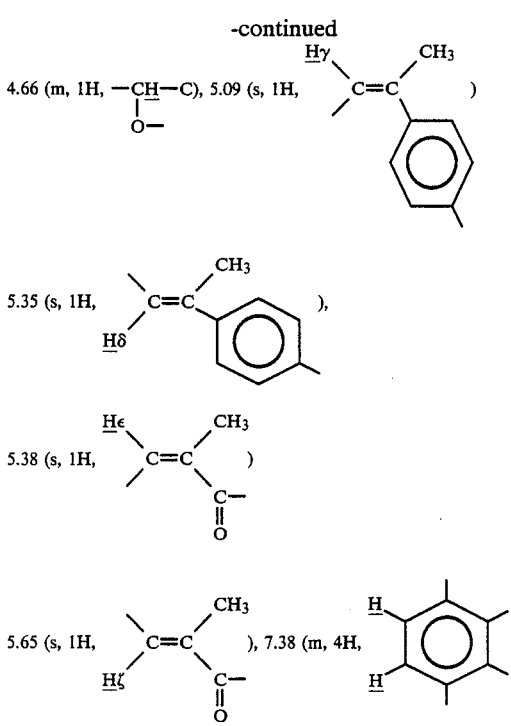

APPLICATION EXAMPLES

Various applications of the present invention will now be described with reference to Application Examples, wherein the parts quoted represent parts by weight and the percentages quoted represent percent by weight.

Application Example 1

30.0 parts of N-(3-isopropenyl-α,α-dimethylbenzyl)-2-methacryloyloxyethyl carbamate, 0.1 part of bis(4-t-butylcyclohexyl) peroxydicarbonate, and 0.1 part of t-butyl peroxyisopropyl carbonate were mixed to form a uniform mixture, and the mixture was deaerated under reduced pressure and cast in a mold composed of a 150 mm×150 mm glass sheet, and a vinyl chloride gasket The cast mixture was then polymerized for 1 hour at 60° C., and further for 1 hour at 120° C., whereafter the platelike polymerized item was removed from the mold. The hardness of the plate, as measured by the pencil hardness method α,α(JIS-K-5401α,α), was found to be 5H, the chemical resistance thereof was good, severing of the plate with a metal severing saw was possible, and grinding of the plate with a lens polisher for machining lenses of spectacles was also possible. The results of these tests, together with the results obtained in Application Examples 2 to 6, are given in Table 1.

The physical properties were measured by the following methods:

(1) Appearance: the platelike polymerized item was visually observed, without magnification.

(2) Light transmittance: was measured in accordance with ASTM D1003.

(3) Surface hardness: a pencil hardness test for paints according to JIS K-5401 was used.

(4) Heat resistance: after the polymerized item was allowed to stand in a hot-air drying chamber at 120° C. for 1 hour, it was visually observed, without magnification. When it was not colored and was free from surface imperfections, it was judged to be O and when it was colored and had surface imperfections, it was judged to be X.

(5) Workability when the polymerized item could be ground by a machine for working lenses of spectacles, it was judged to be O), and when it could not be cut, it was judged to be X.

(6) Chemical resistance: the polymerized item was immersed in isopropanol and toluene at room temperature for 24 hours. When it was not marked by an HB pencil, it was judged as O, whereas when it was marked by an HB pencil, it was judged as X.

Application Example 2

The procedure of Application Example 1 was repeated, except that 30.0 parts of N-(3-isopropenyl-α,α-dimethylbenzyl)-1-acryloyloxypropan-2-yl carbamate were used instead of 30.0 parts of N-(3-isopropenyl-α,α-dimethylbenzyl)-2-methacryloyloxyethyl carbamate, thereby producing a platelike polymerized item.

The pencil hardness of the plate was 5H, the chemical resistance thereof was good, severing of the plate with a metal cutting saw was possible, and grinding of the plate with a lens polisher for working lenses of spectacles was also possible.

Application Example 3

The procedure of Application Example 1 was repeated except that 30.0 parts of N-(4-isopropenyl-α,α-dimethylbenzyl)-2-acryloyl-oxyethyl carbamate were used instead of 30.0 parts of N-(3-isopropenyl-α,α-dimethylbenzyl)-2-methacryloyloxyethyl carbamate, thereby producing a platelike polymerized item.

The pencil hardness of the plate was 5H, the chemical resistance thereof was good, severing of the plate with a metal cutting saw was possible, and grinding of the plate with a lens polisher for working lenses of spectacles was also possible.

Application Example 4

The procedure of Application Example 1 was repeated, except that 30.0 parts of N-(4-isopropenyl-α,α-dimethylbenzyl)-1-methacryloyloxypropan-2-yl carbamate were used instead of 30.0 parts of N-(3-isopropenyl-α,α-dimethylbenzyl)-2-methacryloyloxyethyl carbamate, thereby producing a platelike polymerized item.

The pencil hardness of the plate was 5H, the chemical resistance thereof was good, severing of the plate with a metal cutting saw was possible, and grinding of the plate with a lens polisher for working lenses of spectacles was also possible.

Application Example 5

30.0 parts of N-(3-isopropenyl-α,αdimethylbenzyl)acryloyloxyethyl carbamate, 1.5 parts of styrene, 0.1 part of t-butyl peroxypivalate, and 0.1 part of t-butyl peroxyisopropyl carbonate were mixed uniformly, and the resulting mixture was cast in a mold composed of a 150 mm×150 mm glass sheet, and a vinyl chloride gasket. After polymerization at 70 ° C. for 1 hour, and further at 120° C. for 1 hour, a platelike polymerized item was removed from the mold.

The pencil hardness of the plate was 5H, the chemical resistance thereof was good, severing of the plate with a metal cutting saw was possible, and grinding of the plate with a lens polisher for working lenses of spectacles was also possible.

Application Example 6

30.0 parts of N-(4-isopropenyl-α,α-dimethylbenzyl)-methacryloyloxypropyl carbamate, 1.5 parts of methyl methacrylate, 0.1 part of bis(4-t-butylcyclohexyl) peroxydicarbonate, and 0.1 part of t-butyl peroxyisopropyl carbonate were mixed uniformly, and the resulting mixture was cast in a mold composed of a 150 mm×150 mm glass sheet, and a vinyl chloride gasket. After polymerization at 60° C. for 1 hour, and further at 120° C. for 1 hour, a platelike polymerized item was removed from the mold.

The pencil hardness of the plate was 5H, chemical resistance thereof was good, severing of the plate with a metal cutting saw was possible, and grinding of the plate with a lens polisher for working lenses of spectacles was also possible.

were used instead of 30.0 parts of N-(3-isopropenyl-α,α-dimethylbenzyl)-1,3-dimethacryloyloxypropan-2-yl carbamate, thereby producing a platelike polymerized item.

Application Example 11

30.0 parts of N-(3-isopropenyl-α,α-dimethylbenzyl)-2,2-diacryloyloxymethyl-3-acryloyloxypropyl carbamate, 0.01 part of lauroyl peroxide, and 0.15 part of t-butyl peroxy-2-ethyl hexanoate were mixed uniformly, and the resulting mixture was cast in a mold composed of a 150 mm×150 mm glass sheet, and a

TABLE 1

|  | Application Example 1 | Application Example 2 | Application Example 3 | Application Example 4 | Application Example 5 | Application Example 6 |
| --- | --- | --- | --- | --- | --- | --- |
| Appearance | colorless, transparent | colorless transparent | colorless transparent | colorless transparent | colorless transparent | colorless transparent |
| Light transmittance (%) | 91 | 91 | 91 | 90 | 90 | 91 |
| Surface hardness | 5H | 5H | 5H | 5H | 5H | 5H |
| Heat resistance | O | O | O | O | O | O |
| Workability | O | O | O | O | O | O |
| Chemical resistance | O | O | O | O | O | O |

Application Example 7

30.0 parts of N-(3-isopropenyl-α,α-dimethylbenzyl)-1,3-diacryloyloxypropan-2-yl carbamate, 0.03 part of lauroyl peroxide, and 0.15 part of benzoyl peroxide were mixed uniformly, and the resulting mixture was cast in a mold composed of a 150 mm×150 mm glass sheet, and a vinyl chloride gasket. After polymerization at 55° C. for 1 hour, and further at 130° C. for 1 hour, a platelike polymerized item was removed from the mold. The physical properties thereof are shown in Table 2 together with those of Application Examples 8 to 11.

vinyl chloride gasket. After polymerization at 55° C. for 1 hour, and further at 130° C. for 2 hours, a platelike polymerized item was removed from the mold.

TABLE 2

|  | Application Example 7 | Application Example 8 | Application Example 9 | Application Example 10 | Application Example 11 |
| --- | --- | --- | --- | --- | --- |
| Appearance | colorless, transparent | colorless transparent | colorless transparent | colorless transparent | colorless transparent |
| Light transmittance (%) | 91 | 91 | 91 | 91 | 91 |
| Surface hardness | 9H | 5H | 6H | 9H | 9H |
| Heat resistance | O | O | O | O | O |
| Workability | O | O | O | O | O |
| Chemical resistance | O | O | O | O | O |

Application Example 8

The procedure of Application Example 7 was repeated, except that 30.0 parts of N-(3-isopropenyl-α,α-dimethylbenzyl)-1,3-dimethacryloyloxypropan-2-yl carbamate were used instead of 30.0 parts of N-(3-isopropenyl-α,α-dimethylbenzyl)-1,3-diacryloyloxypropan-2-yl carbamate, the polymerization was effected for 1 hour at 60° C. instead of 55° C., and further for 2 hours at 140° C. instead of 130° C., thereby producing a platelike polymerized item.

Application Example 9

The procedure of Application Example 8 was repeated except that 30.0 parts of N-(3-isopropenyl-α,α-dimethylbenzyl)-1-acryloyloxy-3-methacryloyloxypropan-2-yl carbamate were used instead of 30.0 parts of N-(3-isopropenyl-α,α-dimethylbenzyl)-1,3-dimethacryloyloxypropan2-yl carbamate, thereby producing a platelike polymerized item.

Application Example 10

The procedure of Application Example 8 was repeated except that 30.0 parts of N-(4-isopropenyl-α,α-dimethylbenzyl)-1,3-acryloyloxypropan-2-yl carbamate Application Example 12

0.2 part of benzoyl peroxide was added to 20.0 parts of N-(3-isopropenyl-α,α-dimethylbenzyl)-5-acryloyloxymethylene-2-oxazolidone, they were mixed well, and the mixture deaerated to form a uniform liquid. The liquid was then cast in a mold composed of a 150 mm×150 mm glass sheet, and a vinyl chloride gasket. After polymerization at from 55° C. to 140° C. for 1.5 hours in a hot-air oven for polymerization, a platelike polymerized item was removed from the mold. The physical properties are shown in Table 3 together with those of Application Examples 13 to 15.

Application Example 13

The procedure of Application Example 12 was repeated, except that 20.0 parts of N-(4-isopropenyl-α,α-dimethylbenzyl)-5-acryloyloxymethylene-2-oxazolidone were used instead of 20.0 parts of N-(3-isopropenyl-α,α-dimethylbenzyl)-5-acryloyloxymethylene-2-oxazolidone, thereby producing a platelike polymerized item.

Application Example 14

The procedure of Application Example 12 was repeated, except that 20.0 parts of N-(3-isopropenyl-α,α-dimethylbenzyl)-5-methacryloyloxymethylene-2-oxazolidone were used instead of 20.0 parts of N-(3-isopropenyldimethylbenzyl)-5-acryloyloxymethylene-2-oxazolidone, thereby producing a platelike polymerized item.

Application Example 15

The procedure of Application Example 12 was repeated except that 20.0 parts of N-(4-isopropenyl-α,α-dimethylbenzyl)-5-methacryloyloxymethylene-2-oxazolidone were used instead of 20.0 parts of N-(3-isopropenyl-α,α-dimethylbenzyl)-5-acryloyloxymethylene-2-oxazolidone, thereby producing a platelike polymerized item.

Although the present invention has been described in connection with various preferred embodiments thereof, it is evident that other embodiments thereof will be apparent to those skilled in the art from a reading of the present specification and practice of the invention disclosed herein. Accordingly, it is intended that the true scope and spirit of the invention be indicated by the following claims.

TABLE 3

|  | Application Example 12 | Application Example 13 | Application Example 14 | Application Example 15 |
| --- | --- | --- | --- | --- |
| Appearance | O | O | O | O |
| Surface hardness | 5H | 5H | 4H | 4H |
| Heat resistance | O | O | O | O |
| Chemical resistance | O | O | O | O |
| Workability | O | O | O | O |

What is claimed is:

1. A polyfunctional monomer of the formula (I):

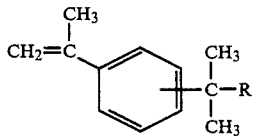

where R is selected from the group consisting of

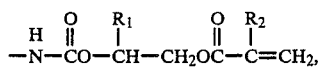

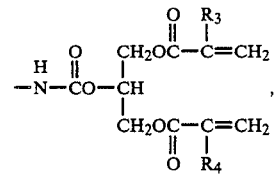

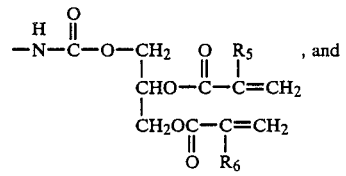

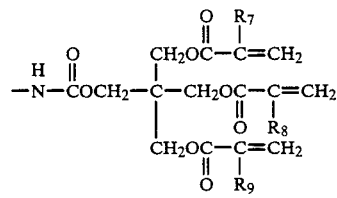

$R_1$ – $R_9$ are each independently selected from the group consisting of hydrogen and a methyl group.

* * * * *